US008431705B2

(12) United States Patent
Grote et al.

(10) Patent No.: US 8,431,705 B2
(45) Date of Patent: Apr. 30, 2013

(54) ONE-POT PREPARATION OF HEXAHYDROISOQUINOLINES FROM AMIDES

(75) Inventors: Christopher W. Grote, Webster Groves, MO (US); Frank W. Moser, Arnold, MO (US); Peter X. Wang, Creve Coeur, MO (US); Gary L. Cantrell, Troy, IL (US); David W. Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 202 days.

(21) Appl. No.: 12/889,484

(22) Filed: Sep. 24, 2010

(65) Prior Publication Data

US 2011/0071299 A1   Mar. 24, 2011

Related U.S. Application Data

(60) Provisional application No. 61/245,295, filed on Sep. 24, 2009.

(51) Int. Cl.
*C07D 217/18* (2006.01)
(52) U.S. Cl.
USPC ........................................................ 546/149
(58) Field of Classification Search ........................ None
See application file for complete search history.

(56) References Cited

U.S. PATENT DOCUMENTS

| 4,521,601 | A  | 6/1985  | Rice           |
| 4,991,391 | A  | 2/1991  | Kosinski       |
| 6,887,999 | B1 | 5/2005  | Likhotvorik    |
| 2007/0244327 | A1 | 10/2007 | Wang et al.    |
| 2009/0247756 | A1 | 10/2009 | Cantrell et al.|

FOREIGN PATENT DOCUMENTS

| CN | 1115318    | 1/1996 |
| CN | 1115318 A  | 1/1996 |
| DE | 922 827    | 1/1955 |
| WO | WO 2006/052430 | 5/2006 |
| WO | WO 2008/073389 A2 | 6/2008 |

OTHER PUBLICATIONS

International Preliminary Report on Patentability for PCT/US2010/05093 dated Mar. 27, 2012.*
Bermejo et al., "Syntheses and Antitumor Targeting G1 Phase of the Cell Cycle of . . . ", Journal of Medicinal Chemistry, 2002, 45, pp. 5058-5068, XP 002302936.
Beyerman et al., "Synthesis of racemic and optically active codeine and morphine via the N-formylnordihydrothebainones", Journal of the Royal Netherlands Chemical Society, 97, 5, May 1978, pp. 127-130.
Beyerman et al., "Synthesis of racemic and of (+)- and (−)-1 methyldihydrothebainone. (Chemistry of opium alkaloids, Part IV)", Recl. Trav. Chim. Pays-Bas, 1976, 75, p. 184-188.
Partial European Search Report dated Feb. 5, 2010.
Farber et al., "A Synthesis of Armepavine and Related Bases. Resolution of (±)-Armepavine", Anales. Asoc. Quim. Argentina, 58, 1970, pp. 133-138.
Farber et al., "Resolution of (±)-armepavine", Chemistry and Industry, Jan. 13, 1968, pp. 57-58.
Finkelstein, "The Synthesis of dl-Claurine", J. Am. Chem. Soc., 73(2), 1951, pp. 550-553, XP 002565009.
Greene et al., "Protection for Phenols", Protective Groups in Organic Synthesis, 3$^{rd}$, Ed., c1999, pp. 249-257and 266-269.
Huang et al., "Synthesis of (+−)-Glaucine and (+−)-Neospirodienone via an One-Pot Bischler-Napieralski Reaction and Oxidative Coupling by a Hypervalent Iodine Reagent", Helvetica Chimica Acta 2004 CH, vol. 887, No. 1, 2004, pp. 167-174, XP002476119.
Kametani et al., "Syntheses of heterocyclic compounds. CLXXV. Coclaurine and related compounds. 2. Syntheses of 7-benzyloxy-1,2,3,4-tetrahydro-1-(p-hydroxybenzyl)-6-methoxy-2-methylisoquinoline", Yakugaku Zasshi—Journal of the Pharmaceutical Society of Japan, Japan Science and Technology Information Aggregator, Electronic, JP, 87(7), 1967, pp. 757-760, XP 009127995.
Kashdan et al., "Synthesis of 1,2,3,4-Tetrahydroisoquinolines", J. Org. Chem., 1982, 47, pp. 2638-2643.
Kitamura et al., "General Asymmetric Synthesis of Isoquinoline Alkaloids. Enantioselective Hydrogenation of enamides Catalyzed by BINAP-Ruthenium(II) Complexes", J. Org. Chem., 1994, 59, pp. 297-310, XP 002050844.
Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584, XP 002478376.
Lespagnol et al., "Etude de dihydro-isoquinoléines iodées", Chimie Thérapeutique, Mai-Juin, 1968, No. 3, pp. 173-175.
Lespagnol et al., "Préparation d'amides de l'homovératrylamine et d'acides iodophénylacétiques substitués", Chim. Therap., 1965, 1, pp. 14-16.
Lespagnol et al., "Preparation of amides from the homoveratrylamine and iodephenylacetic substituted acids", Chim. Therap., 1965, pp. 14-16, English Translation by FAST-TRANS.
Meuzelaar et al., "Chemistry of Opium Alkaloids, 45 Improvements in the Total Synthesis of Morphine", Eur. J. Org. Chem., 1999, pp. 2315-2321.
Passarella et al., "A Convenient Synthesis of Δ$^{7,8}$-Morphinan-6-one and Its Direct Oxidation to 14-Hydroxy-Δ$^{7,8}$-morphinan-6-one", Bioorganic & Medicinal Chemistry Letters, 2002, 12, pp. 1981-1983, XP 002553601.
Rice et al., "Synthetic Opium Alkaloids and Erivatives. A Short Total Synthesis . . . ", J. Org. Chem., 1980, 45, pp. 3135-3137, XP 002396231.
Sam et al., "Modified Synthesis of dl-N-Norarmepavine and dl-Armepavine", J. Pharmaceutical Sciences, 1967, pp. 906-908, XP 002567370.
Sheth et al., "Synthesis of N-(3',4'-Dimethoxy-5'-bromophenethyl)-2-(4"-hydrioxyphenyl)-acetamide & Allied Products", Indian Journal of Chemistry, vol. 15B, Jul. 1977, pp. 595-598.

(Continued)

*Primary Examiner* — Zinna Northington Davis

(57) ABSTRACT

The present invention provides an efficient process for the preparation of hexahydroisoquinolines from amides. In particular, the invention provides a good yielding, one-pot process for the synthesis of hexahydroisoquinolines.

20 Claims, No Drawings

OTHER PUBLICATIONS

Small et al., "The Addition of Organomagnesium Halides to Pseudocodeine Types. IV. Nuclear-Substituted Morphine Derivatives", Contribution from the Cobb Chemical Laboratory, University of Virginia, pp. 204-232.

Tolkachev et al., "Synthetic studies in the curare alkaloids area, XVI. Synthesis of 1-(3-bromo-4-methoxybenzyl)-67-dimethoxy-8-bromo-N-methyl-1,2,3,4-tetrahydroisoquinoline", Zhurnal Obshechei Khimii, Izdatel'Stvo Nauka, Sanky-Peterburgskoe Otdelenie, Russian Federation, 36(10), 1966, pp. 1767-1772, XP009127991.

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772, English Translation proviced by FAST-TRANS.

Tomita et al., Studies on the Alkaloids of Menispermaceous Plants., Chem. Pharm. Bull., 15(22), 1967, pp. 1996-1999, XP 002567369.

Uematsu et al., "Asymmetric Transfer Hydrogenation of Imines", J. Am. Chem. Soc., 1996, 118, pp. 4916-4917.

H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands.

Venkov et al., "Synthesis of isoquinolines from 2-phenylethylamines, amides, nitriles and carboxylic acids in polyphosphoric acid", Tetrahedron Sep. 9, 1996 GB, vol. 52, No. 37, Sep. 9, 1996, pp. 12299-12308, XP 002476120.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Kitamura et al., "General Asymmetric Synthesis of Isoquinoline Alkaloids, Enantioselective Hydrogenation of enamides Catalyzed by BINAP-Ruthenium (II) Comlexes", Journal of Organic Chemistry, 59(2), 1994, pp. 297-310, XP 002609525.

* cited by examiner

ONE-POT PREPARATION OF HEXAHYDROISOQUINOLINES FROM AMIDES

CROSS REFERENCE TO RELATED APPLICATIONS

This application claims the benefit of U.S. Provisional Application No. 61/245,295 filed Sep. 24, 2009, which is incorporated herein in its entirety.

FIELD OF THE INVENTION

The present invention generally relates to the processes for the synthesis of intermediates used to prepare morphinans. More specifically, the invention relates to the synthesis of hexahydroisoquinolines from amides via a one-pot process.

BACKGROUND OF THE INVENTION

Hexahydroisoquinoline and its derivatives are important synthetic intermediates to many morphinan compounds including buprenorphine, codeine, etorphine, hydrocodone, hydromorphone, morphine, nalbuphine, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone and naltrexone are opiate receptor antagonists; they are used for reversal of narcotic/respiratory depression due to opiate receptor agonists.

Currently available processes for the preparation of hexahydroisoquinolines tend to be inefficient and low yielding because intermediates are isolated after each reaction step. Given the commercial importance of hexahydroisoquinolines, a need exists for streamlined, efficient processes for their preparation.

SUMMARY OF THE INVENTION

Among the various aspects of the present invention is the provision of an efficient one-pot process for the preparation of a hexahydroisoquinoline comprising Formula (IV). The process comprises (a) contacting a compound comprising Formula (I) with $POCl_3$ to form a compound comprising Formula (II), (b) contacting the compound comprising Formula (II) with an asymmetric catalyst and a hydrogen donor comprising a formate ion to form a compound comprising Formula (III); and (c) contacting the compound comprising Formula (III) with an alkali metal and an electron source to form the compound comprising Formula (IV) according to the following reaction scheme:

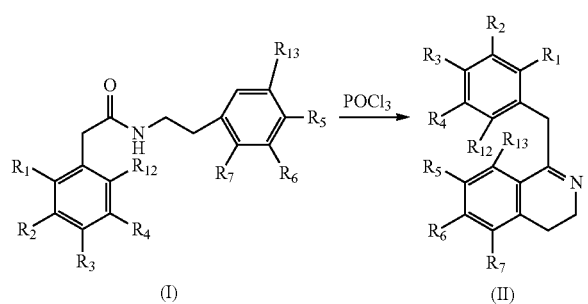

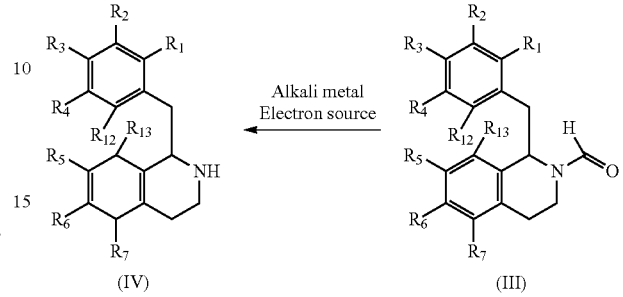

wherein:
$R_1$, $R_5$, and $R_7$ are independently selected from the group consisting of hydrogen, hydrocarbyl, substituted hydrocarbyl, and $-OR_{111}$;
$R_2$, $R_4$, and $R_6$ are independently selected from the group consisting of hydrogen, hydrocarbyl, substituted hydrocarbyl, halo, and $-OR_{211}$;
$R_3$ is selected from the group consisting of hydrogen, hydrocarbyl, substituted hydrocarbyl, and $-OR_{211}$;
$R_{12}$ and $R_{13}$ are independently selected from the group consisting of hydrogen, hydrocarbyl, substituted hydrocarbyl, halo, and $-OR_{111}$;
$R_{111}$ is selected from the group consisting of hydrogen, hydrocarbyl, and substituted hydrocarbyl;
$R_{211}$ is selected from the group consisting of hydrogen, hydrocarbyl, $-C(O)R_{212}$, $-C(O)C(R_{212})_3$, $-C(O)NHR_{212}$, and $-SO_2R_{212}$; and
$R_{212}$ is selected from the group consisting of hydrocarbyl and substituted hydrocarbyl.

Other aspects and features of the invention are described in more detail below.

DETAILED DESCRIPTION

The present invention provides an improved synthetic process for the preparation of optically active hexahydroisoquinolines. In particular, the process is conducted in one reaction vessel without the isolation of intermediate compounds. The process comprises a cyclization of an amide to form a dihydroisoquinoline, asymmetric reduction of the dihydroisoquinoline to form an optically active tetrahydroisoquinoline, and then reduction of the tetrahydroisoquinolines to produce the hexahydroisoquinoline. The process, therefore, produces hexahydroisoquinolines in good yield with good asymmetric control.

Process for the Preparation of Hexahydroisoquinolines Comprising Formula (IV)

The present invention provides an efficient process for the preparation of hexahydroisoquinolines comprising Formula (IV) from amides comprising Formula (I). Specifically, the process comprises a cyclization reaction (step A) wherein the amide comprising Formula (I) is contacted with $POCl_3$ to form a 3,4-dihydroisoquinoline comprising Formula (II). The process further comprises an imine reduction (step B) wherein the compound comprising Formula (II) is contacted with an asymmetric catalyst and a hydrogen donor comprising a formate ion to form an optically active N-formyl tetrahydroisoquinoline comprising Formula (III). Lastly, the process comprises a Birch reduction (step C) wherein the compound comprising Formula (III) is contacted with an alkali metal and an electron source to form the hexahydroisoquinoline comprising Formula (IV). For purposes of illustration, Reaction Scheme 1 depicts the synthesis of the compound comprising Formula (IV) in accordance with this aspect of the invention:

Reaction Scheme 1:

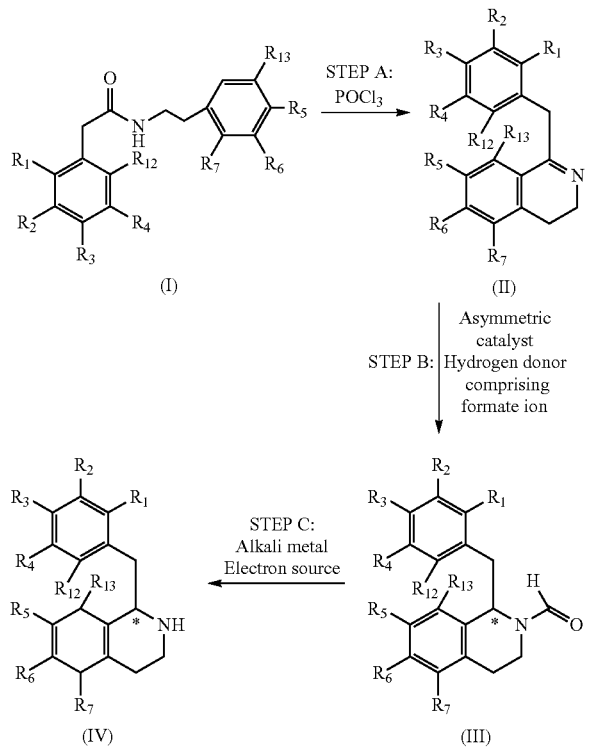

wherein:
$R_1$, $R_5$, and $R_7$ are independently selected from the group consisting of hydrogen, hydrocarbyl, substituted hydrocarbyl, and —$OR_{111}$;
$R_2$, $R_4$, and $R_6$ are independently selected from the group consisting of hydrogen, hydrocarbyl, substituted hydrocarbyl, halo, and —$OR_{211}$;
$R_3$ is selected from the group consisting of hydrogen, hydrocarbyl, substituted hydrocarbyl, and —$OR_{211}$;
$R_{12}$ and $R_{13}$ are independently selected from the group consisting of hydrogen, hydrocarbyl, substituted hydrocarbyl, halo, and —$OR_{111}$;
$R_{111}$ is selected from the group consisting of hydrogen, hydrocarbyl, and substituted hydrocarbyl;
$R_{211}$ is selected from the group consisting of hydrogen, hydrocarbyl, —$C(O)R_{212}$, —$C(O)C(R_{212})_3$, —$C(O)NHR_{212}$, and —$SO_2R_{212}$;
$R_{212}$ is selected from the group consisting of hydrocarbyl and substituted hydrocarbyl; and
* indicates a chiral carbon atom.

In one embodiment, $R_3$ is —$OR_{211}$, wherein $R_{211}$ is selected from the group consisting of hydrogen, alkyl, —$C(O)R_{212}$, —$C(O)C(R_{212})_3$, —$C(O)NHR_{212}$, and —$SO_2R_{212}$, and wherein $R_{212}$ is selected from the group consisting of alkyl and aryl. In another embodiment, $R_4$ is —$OR_{211}$, wherein $R_{211}$ is selected from the group consisting of hydrogen, alkyl, —$C(O)R_{212}$, —$C(O)C(R_{212})_3$, —$C(O)NHR_{212}$, and —$SO_2R_{212}$, and wherein $R_{212}$ is selected from the group consisting of alkyl and aryl. In a further embodiment, $R_6$ is —$OR_{211}$, wherein $R_{211}$ is selected from the group consisting of hydrogen, alkyl, —$C(O)R_{212}$, —$C(O)C(R_{212})_3$, —$C(O)NHR_{212}$, and —$SO_2R_{212}$, and wherein $R_{212}$ is selected from the group consisting of alkyl and aryl. In still another embodiment, $R_{12}$ is selected from the group consisting of alkyl, allyl, benzyl, and halo. In an alternate embodiment, $R_{212}$ is methyl.

In an exemplary embodiment, $R_1$, $R_2$, $R_5$, $R_7$, $R_{12}$, and $R_{13}$ are hydrogen, $R_3$ and $R_6$ are methoxy, and $R_4$ is selected from the group consisting of hydroxyl, —$OC(O)CH_3$, —$C(O)C(CH_3)_3$, —$OC(O)Ph$, and —$OSO_2CH_3$.

(I) Step A

Cyclization of Amides to Form 3,4-Dihydroisoquinolines

The first step of the process comprises a Bischler-Napieralski cyclization of the amide comprising Formula (I) to form a 3,4-dihydroisoquinoline comprising Formula (II). The process commences with formation of a reaction mixture by combining the amide comprising Formula (I) with $POCl_3$ (also called phosphorous oxychloride). The amount of $POCl_3$ used in the process can and will vary. In general, the molar ratio of the compound comprising Formula (I) to $POCl_3$ may range from about 1:0.5 to about 1:5. In various embodiments, the molar ratio of the compound comprising Formula (I) to $POCl_3$ may range from about 1:0.5 to about 1:1, from about 1:1 to about 1:2, or from about 1:2 to about 1:5. In preferred embodiments, the molar ratio of the compound comprising Formula (I) to $POCl_3$ may range from about 1:0.9 to about 1:1.1, or more preferably the ratio may be about 1:1.

(a) Solvent

The reaction mixture also comprises a solvent. Typically, the solvent will be an aprotic solvent. Non-limiting examples of suitable aprotic solvents include toluene, xylene, acetonitrile, ethyl acetate, propyl acetate, tetrahydrofuran, or combinations thereof. In an exemplary embodiment, the solvent may be toluene. In general, the weight ratio of the solvent to the compound comprising Formula (I) will range from about 0.1:1 to about 100:1. In various embodiments, the weight ratio of the solvent to the compound comprising Formula (I) may range from about 0.1:1 to about 0.5:1, from about 0.5:1 to about 5:1, from about 5:1 to about 20:1, or from about 20:1 to about 100:1. In a preferred embodiment, the weight ratio of the solvent to the compound comprising Formula (I) may range from about 0.1:1 to about 10:1. In preferred embodiments, the weight ratio of the solvent to the compound comprising Formula (I) may range from about 0.5:1 to about 10:1, or more preferably the ratio may be about 0.7:1 to about 2:1.

In certain embodiments, the reaction may be performed under anhydrous conditions. Suitable anhydrous conditions may be obtained, for example, by removal of water by distillation or by addition of a water-scavenging agent. Removal of water by distillation may occur at discrete time points during the reaction or it may be continuous. For example, use of a Dean-Stark trap provides for continuous removal of water. Also, water may be removed from the reaction mixture by contact with a water scavenger. The water scavenger may be added separately from the other components of the reaction mixture or, alternatively, it may be pre-mixed with one of the components and the mixture is then combined with the remaining components. In general, the water scavenger is preferably a composition that absorbs the water.

(b) Reaction Conditions

The temperature of the reaction can and will vary depending upon the nature of the compound comprising Formula (I), the amount of $POCl_3$ used in the reaction, and the solvent. For example, compounds comprising Formula (I) in which $R_4$ is an oxygen-protecting group may be reacted at lower temperatures than those in which $R_4$ is hydroxyl. Additionally, reaction mixtures containing greater amounts of $POCl_3$ may be reacted at lower reaction temperatures. In general, the reaction will be conducted at a temperature ranging from about 20° C. to about 100° C. In certain embodiments, the temperature of the reaction may range from about 20° C. to about 40° C., from about 40° C. to about 70° C., or from about 70° C. to about 100° C. In a preferred embodiment, the temperature of the reaction may range from about 20° C. to about 40° C. In an exemplary embodiment, the temperature of the reaction may be about room temperature (i.e., from about 22° C. to about 25° C.). The reaction is typically conducted under ambient atmosphere and pressure.

In general, the reaction is allowed to proceed for a sufficient period of time until the reaction is substantially complete, as determined by any method known to one skilled in the art, such as chromatography (e.g., HPLC). The duration of the reaction may range from about one hour to about 48 hours. In some embodiments, the reaction may be allowed to proceed for about 1 hour, about 2 hours, about 4 hours, about 8 hours, about 12 hours, about 18 hours, about 24 hours, about 36 hours, or about 48 hours. In a preferred embodiment, the duration of the reaction may be about 1 hour. In this context, a "completed reaction" generally means that the reaction mixture contains a significantly diminished amount of the compound comprising Formula (I). Typically, the amount of the compound comprising Formula (I) remaining in the reaction mixture may be less than about 3%, and preferably less than about 1%.

The yield of the compound comprising Formula (II) can and will vary. Typically, the yield of the compound comprising Formula (II) will be at least about 60%. In various embodiments, the yield of the compound comprising Formula (II) may range from about 60% to about 70%, from about 70% to about 80%, or from about 80% to about 90%. In still another embodiment, the yield of the compound comprising Formula (II) may be greater than about 90%, or greater than about 95%.

Upon completion of the reaction, the solvent in the reaction mixture may be removed by distillation, solvent displacement, or another process known to those of skill in the art. Importantly, the compound comprising Formula (II) is not isolated as a solid.

(II) Step B

Asymmetric Reduction of 3,4-Dihydroisoquinolines

The next step of the process comprises a reduction of the imine moiety in the dihydroisoquinoline comprising Formula (II) to produce a tetrahydroisoquinoline comprising Formula (III). This imine reduction forms a chiral center in the tetrahydroisoquinoline and occurs in an asymmetric environment. Accordingly, the process of the invention uses an asymmetric catalyst to provide an asymmetric environment for the reduction of the imine moiety. The asymmetric catalyst comprises a metal or a metal source and a chiral ligand. Typically, the ratio of the metal or metal complex to the chiral ligand in the asymmetric catalyst is about 1:1.

(a) Asymmetric Catalyst

A variety of metal or metal sources are suitable for use in the process of the invention. The metal or metal source may be ruthenium, a ruthenium complex, osmium, an osmium complex, rhodium, a rhodium complex, iridium, an iridium complex, palladium, a palladium complex, platinum, a platinum complex, or combinations thereof. The valence of the transition metal may vary. For example, non-limiting examples of suitable transition metals include ruthenium(II), ruthenium(III), ruthenium(IV), osmium(II), osmium(III), osmium(IV), rhodium(I), rhodium(III), iridium(III), iridium(IV), palladium(II), palladium(IV), platinum(II), and platinum(IV).

In preferred embodiments, the transition metal complex may be dichloro(arene)Ru(II) dimer, dichloro(pentamethylcyclopentadienyl)Rh(II) dimer, BINAP-Ru(II) diacetate, BINAP-Ru(II) dichloride, BINAP-Ru(II) dibromide, BINAP-Ru(II) diiodide, [RuCl((R or S)BINAP)($C_6H_6$)]Cl, dichloro(pentamethylcyclopentadienyl)iridium(III) dimer, Ru(III) chloride, $RuCl_3$ hydrate, Ru(III) acetylacetonate, tetraalkylammonium $RuCl_4$, or pyridinium $RuCl_4$. In an exemplary embodiment, the transition metal complex may be dichloro(p-cymene)Ru(II) dimer.

The chiral ligand of the asymmetric catalyst may be a mono- or bidentate nitrogen donor, a phosphorous donor ligand, an oxygen donor ligand, a cyclopentadienyl ligand, an arena ligand, an olefin ligand, an alkyne ligand, a heterocycloalkyl ligand, a heteroaryl ligand, a hydride ligand, an alkyl ligand, or a carbonyl ligand. These catalysts are sometimes referred to as Noyori catalysts, and are more fully described in, for example, U.S. Pat. No. 5,693,820 (Helmchen et al.) and R. Noyori et al., *Asymmetric Catalysts by Architechtural and Functional Molecular Engineering: Practical Chemo-and Stereoselective Hydrogenation of Ketones*, Agew. Chem. Int. Ed. 2001, 40, pp. 40-73. In one example, the chiral ligand may comprise Formula 670, 680, 690, or 700, as shown below:

wherein:
- $R_{671}$, $R_{672}$, $R_{673}$, $R_{681}$, $R_{691}$, $R_{692}$, $R_{701}$, and $R_{702}$ are independently alkyl or aryl;
- $R_{691}$ and $R_{692}$ of Formula 690 and $R_{701}$ and $R_{702}$ of Formula 700, and the carbon atoms to which they are attached, may optionally form a cyclic or bicyclic compound; and
- * indicates a chiral carbon atom.

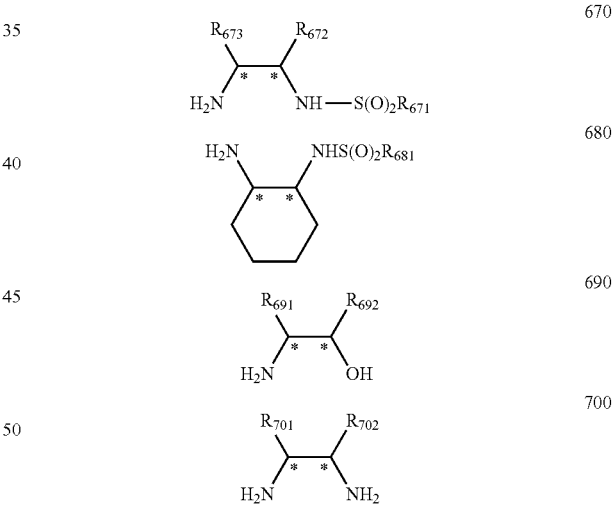

The configuration of the chiral carbons in the ligands comprising Formulas 670, 680, 690, or 700 may be RR, RS, SR, or SS.

In one embodiment, the ligand comprises Formula 670, and $R_{672}$ and $R_{673}$ are each phenyl and $R_{671}$ is aryl. In another example of this embodiment, $R_{671}$ is tolyl, mesityl, or naphthyl. In an alternative embodiment, the ligand comprises Formula 680 and $R_{681}$ is tolyl, mesityl, 2,4,6-triisopropylphenyl, or naphthyl. In another example, the ligand comprises Formula 690, and $R_{691}$ and $R_{692}$ are hydrogen thus forming the compound, aminoethanol. In another embodiment, the ligand corresponds to Formula 700, and $R_{701}$ and $R_{702}$ are hydrogen thus forming the compound, ethylenediamine. In an alternative example, the ligand comprises Formula 690, and $R_{691}$ and $R_{692}$ are selected to form the

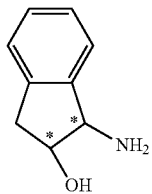 [SMILES: NC1c2ccccc2CC1O]

following compound:

In a preferred embodiment, the chiral ligand may be p-toluenesulfonyl-1,2-diphenylethylenediamine, (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

Suitable ruthenium or rhodium asymmetric catalysts include the following:

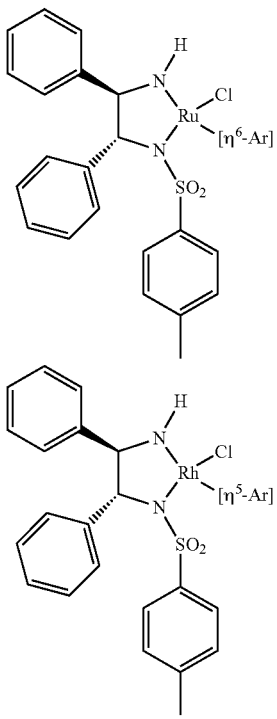

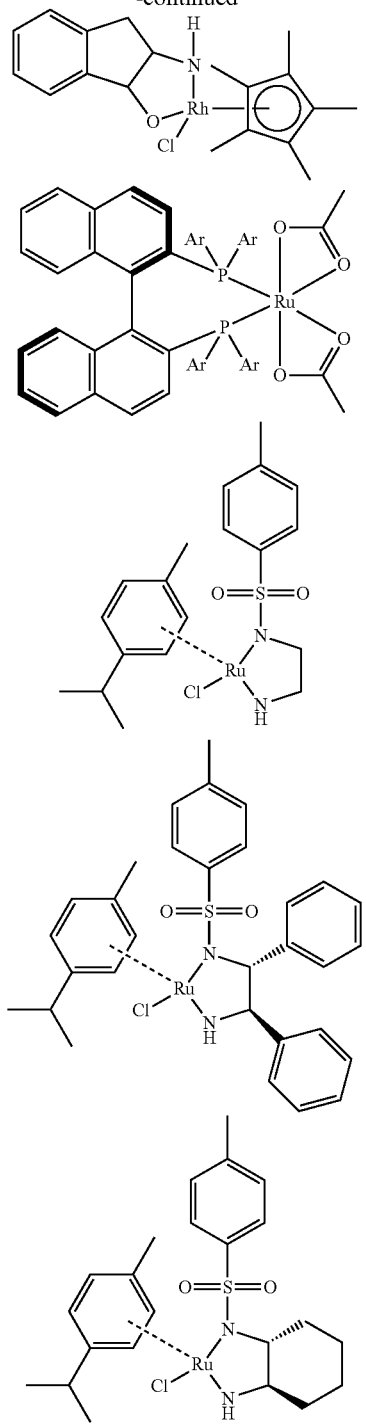

The weight ratio of the asymmetric catalyst to the compound comprising Formula (II) can and will vary. In general, the weight ratio of the asymmetric catalyst to the compound comprising Formula (II) will range from about 0.001:1 to about 0.1:1. In some embodiments, the weight ratio of the asymmetric catalyst to the compound comprising Formula (II) may range from about 0.001:1 to about 0.01:1, or from about 0.01:1 to about 0.1:1. In a preferred embodiment, the weight ratio of the asymmetric catalyst to the compound comprising Formula (II) may range from about 0.005:1 to about 0.02:1. In an exemplary embodiment, the weight ratio of the asymmetric catalyst to the compound comprising Formula (II) may be about 0.01:1.

(b) Hydrogen Donor

In addition to the compound comprising Formula (II) and the asymmetric catalyst, the reaction mixture also comprises a hydrogen donor comprising a formate ion. Non-limiting example of suitable hydrogen donors include formic acid, an inorganic salt of formic acid, an organic salt of formic acid, or a mixture of formic acid and an organic base. Suitable inorganic salts of formic acid include, but are not limited to, calcium formate, cesium formate, lithium formate, magnesium formate, potassium formate, and sodium formate. Non-limiting examples are suitable organic salts of formic acid include ammonium formate, ethyl formate, methyl formate, amine formate, butyl formate, propyl formate, triethyl orthoformate, triethyl orthoformate, triethylammonium formate, trimethylammonium formate, and the like. Suitable organic bases for combining with formic acid include, but are not limited to, pyridine, triethylamine, diisopropylethylamine, N-methylmorpholine, and N,N-dimethylaminopyridine. In a preferred embodiment, the hydrogen donor comprises a mixture of formic acid and an organic base. In an exemplary embodiment, the hydrogen donor comprises a mixture of formic acid and triethylamine. Typically, the molar ratio of formic acid to triethylamine is about 2:1.

The molar ratio of the compound comprising Formula (II) to the hydrogen donor can and will vary. In general, the molar ratio of the compound comprising Formula (II) to the hydrogen donor will range from about 1:1 to about 1:20. In various embodiments, the molar ratio of the compound comprising Formula (II) to the hydrogen donor may range from 1:1 to about 1:3, from about 1:3 to about 1:10, or from about 1:10 to about 1:20. In preferred embodiments, the molar ratio of the compound comprising Formula (II) to the hydrogen donor may range from 1:5 to about 1:10. In an exemplary embodiment in which the hydrogen donor comprises formic acid and triethylamine, the molar ratio of the compound comprising Formula (II) to formic acid may range from about 1:4 to about 1:6, and the molar ratio of the compound comprising Formula (II) to triethylamine may range from about 1:2 to about 1:3.

(c) Solvent

The imine reduction reaction mixture also comprises a solvent. Typically, the solvent is an aprotic, polar solvent. Non-limiting examples of suitable aprotic solvents include acetonitrile, dimethylsulfoxide, tetrahydrofuran, halocarbons (e.g., dichloromethane, chloroform), dimethylformamide, dimethylacetamide, N-methylpyrrolidinone, or combinations thereof. Preferably, the solvent may be acetonitrile.

In general, the weight ratio of the solvent to the compound comprising Formula (II) will range from about 0.1:1 to about 100:1. In various embodiments, the weight ratio of the solvent to the compound comprising Formula (II) may range from about 0.1:1 to about 0.5:1, from about 0.5:1 to about 5:1, from about 5:1 to about 20:1, or from about 20:1 to about 100:1. In preferred embodiments, the weight ratio of the solvent to the compound comprising Formula (II) may range from about 0.5:1 to about 10:1, or more preferably from about 2:1 to about 4:1.

(d) Reaction Conditions

The temperature of the reaction can and will vary depending upon the reactants. In general, the reaction will be conducted at a temperature ranging from about 20° C. to about 100° C. In certain embodiments, the temperature of the reaction may range from about 20° C. to about 40° C., from about 40° C. to about 70° C., or from about 70° C. to about 100° C. In a preferred embodiment, the temperature of the reaction may range from about 20° C. to about 30° C. In an exemplary embodiment, the temperature of the reaction may be about room temperature (i.e., from about 22° C. to about 25° C.). Typically, the reaction is conducted under ambient atmosphere and pressure.

In general, the reaction is allowed to proceed for a sufficient period of time until the reaction is substantially complete, as determined by any method known to one skilled in the art, such as chromatography (e.g., HPLC). Typically, the duration of the reaction will range from about 4 hours to about 24 hours. In some embodiments, the reaction may be allowed to proceed for about 4 hours, about 8 hours, about 10 hours, about 12 hours, about 16 hours, about 20 hours, or about 24 hours. In a preferred embodiment, the duration of the reaction may be about 16 hours. In this context, a "completed reaction" generally means that the reaction mixture contains a significantly diminished amount of the compound comprising Formula (II). Generally, the amount of the compound comprising Formula (II) remaining in the reaction mixture may be less than about 3%, and preferably less than about 1%.

Asymmetric reduction of the compound comprising Formula (II) produces an N-formyl tetrahydroisoquinoline comprising Formula (III). In some embodiments, the reduction may also produce a non-formylated tetrahydroisoquinoline comprising Formula (III'):

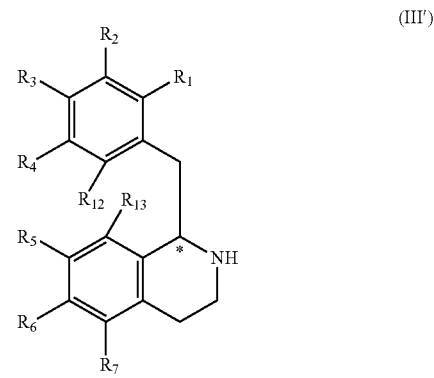

(III')

wherein $R_1$, $R_2$, $R_3$, $R_4$, $R_5$, $R_6$, $R_7$, $R_{12}$, and $R_{13}$ are as defined above in Reaction Scheme 1.

The weight ratio of the compound comprising Formula (III) to the compound comprising Formula (III') can and will vary. For example, ratio of the compound comprising Formula (III) to the compound comprising Formula (III') may range from about 0.5:1 to about 10:1. In some embodiments, the ratio of the compound comprising Formula (III) to the compound comprising Formula (III') may range from about 0.5:1 to about 2:1, from about 2:1 to about 4:1, from about 4:1 to about 6:1, from about 6:1 to about 8:1, or from about 8:1 to about 10:1.

The yield of the compound comprising Formula (III), as well as the compound comprising Formula (III'), if present, can and will vary. Typically, the yield of the compounds) will be at least about 60%. In various embodiments, the yield may range from about 60% to about 70%, from about 70% to about 80%, or from about 80% to about 90%. In still another embodiment, the yield may be greater than about 90%, or greater than about 95%.

Upon completion of the imine reduction, the tetrahydroisoquinoline products typically precipitate out of solution and may be recovered by methods known in the art. For example, the products may be collected by filtration of the reaction mixture followed by washing the precipitate with a solvent.

(III) Step C

Reduction of Tetrahydroisoquinolines

The final step of the process comprises a Birch reduction of the compound comprising Formula (III), and the compound comprising Formula (III'), if present, to form the hexahydroisoquinoline comprising Formula (IV). The Birch reduction is generally effected using a reducing agent.

(a) Reducing Agent

A variety of reducing agents are suitable for use in this process. Exemplary reducing agents comprise an alkali metal and an electron source. Suitable alkali metals include lithium, sodium, potassium, or combinations thereof. Non-limiting examples of suitable electron sources include liquid ammonia, methylamine, ethylamine, ethylenediamine, or combinations thereof. In an exemplary embodiment, the reducing agent for the Birch reduction comprises lithium metal and liquid ammonia.

The molar ratio of the compound comprising Formula (III) to the alkali metal may range from about 1:2 to about 1:20. In various embodiments, the molar ratio of the compound comprising Formula (III) to the alkali metal may be about 1:2, about 1:4, about 1:6, about 1:8, about 1:10, about 1:12, about 1:14, about 1:16, about 1:18, or about 1:20. In preferred embodiments, the molar ratio of the compound comprising Formula (III) to the alkali metal may range from about 1:2 to about 1:15. In exemplary embodiments, the molar ratio of the compound comprising Formula (III) to the alkali metal may range from about 1:3 to about 1:10.

The amount the electron source combined with the compound comprising Formula (III) and the alkali metal can and will vary depending upon, for example, the type of electron source. In embodiments in which the electron source is liquid ammonia, the weight to volume ratio of the compound comprising Formula (III) to liquid ammonia may range from about 1:2 to about 1:50 (g/mL). Stated another way, for each gram of the compound comprising Formula (III), about 2 mL to about 50 mL of liquid ammonia may be added to the reaction mixture. In preferred embodiments, the weight to volume ratio of the compound comprising Formula (III) to liquid ammonia may range from about 1:2 to about 1:15 (g/mL). In exemplary embodiments, the weight to volume ratio of the compound comprising Formula (III) to liquid ammonia may range from about 1:3 to about 1:10 (g/mL).

(b) Solvent

The Birch reduction reaction mixture also comprises a solvent mixture. The solvent mixture typically comprises a protic solvent and an aprotic solvent. Non-limiting examples of suitable protic solvents include ethyl alcohol, isopropyl alcohol, n-propyl alcohol, isobutyl alcohol, n-butyl alcohol, s-butyl alcohol, and t-butyl alcohol. Suitable aprotic solvents include, but are not limited to, diethoxymethane, diethyl ether, diisopropyl ether, 1,2-dimethoxyethane, dimethoxymethane, 1,4-dioxane, di-tert-butyl ether, ethyl tert-butyl ether, ethyl acetate, ethylene oxide, bis(2-methoxyethyl)ether, t-butyl methyl ether, methyl tert-butyl ether, tetrahydrofuran, and 2-methyl tetrahydrofuran. In preferred embodiments, the solvent mixture may comprise t-butyl alcohol and tetrahydrofuran, or more preferably the solvent mixture may comprise isopropyl alcohol and tetrahydrofuran.

The weight ratio of the protic solvent to the aprotic solvent in the solvent mixture may range from about 1:2 to about 1:10. For example, the weight ratio of the protic solvent to the aprotic solvent in the solvent mixture may range from about 1:2 to about 1:3, about 1:3 to about 1:5, about 1:5 to about 1:7, or from about 1:7 to about 1:10. In a preferred embodiment, the weight ratio of the protic solvent to the aprotic solvent in the solvent mixture may range from about 1:5 to about 1:6.

In general, the weight ratio of the solvent mixture to the compound comprising Formula (III) will range from about 0.1:1 to about 100:1. In various embodiments, the weight ratio of the solvent mixture to the compound comprising Formula (III) may range from about 0.1:1 to about 0.5:1, from about 0.5:1 to about 5:1, from about 5:1 to about 20:1, or from about 20:1 to about 100:1. In a preferred embodiment, the weight ratio of the solvent mixture to the compound comprising Formula (III) may range from about 1:1 to about 10:1, or more preferably from about 3:1 to about 6:1.

(c) Reaction Conditions

Depending on the reagents used, the Birch reduction occurs at a temperature ranging from about −80° C. to about 10° C. When liquid ammonia is used as a reagent, the reduction takes place at about −80° C. to about −35° C. When methylamine or ethylamine is used as a reagent, the reduction takes place at a temperature from about −10° C. to about 10° C. In preferred embodiments in which the reducing agent comprises liquid ammonia and lithium metal, the temperature of the reaction may range from about −70° C. to about −60° C. or from about −55° C. to about −45° C. Generally, the reaction is conducted under ambient atmosphere and pressure.

In general, the Birch reduction is allowed to proceed for a sufficient period of time until the reaction is substantially complete, as determined by any method known to one skilled in the art. In general, the duration of the reaction will range from about 10 minutes to about 4 hours. In various embodiments, the reaction may be allowed to proceed for about 10 minutes, about 20 minutes, about 30 minutes, about 40 minutes, about 1 hour, about 1.5 hours, about 2 hours, about 3 hours, or about 4 hours. In a preferred embodiment, the reaction may proceed for about 30 minutes. A "completed reaction" generally means that the reaction mixture contains a significantly diminished amount of the compound comprising Formula (III). Typically, the amount of the compound comprising Formula (III) remaining in the reaction mixture may be less than about 3%, and preferably less than about 1%.

The yield of the hexahydroisoquinoline comprising Formula (IV) can and will vary. Typically, the yield of the compound comprising Formula (IV) will be at least about 60%. In various embodiments, the yield of the compound comprising Formula (IV) may range from about 60% to about 70%, from about 70% to about 80%, or from about 80% to about 90%. In still another embodiment, the yield of the compound comprising Formula (IV) may be greater than about 90%.

In some embodiments, the Birch reduction may also produce an N-methylated compound comprising Formula (IV):

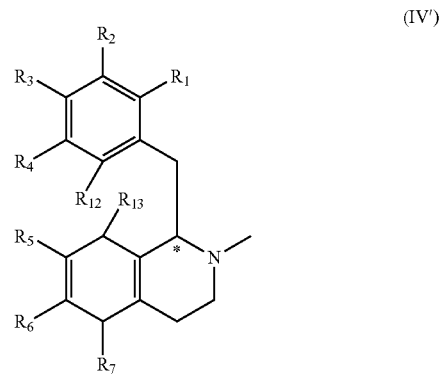

wherein $R_1$, $R_2$, $R_3$, $R_4$, $R_5$, $R_6$, $R_7$, $R_{12}$, and $R_{13}$ are as defined above in Reaction Scheme 1.

The ratio of the compound comprising Formula (IV) to the compound comprising Formula (IV') can and will vary depending on the reactants and the reaction conditions. In general, the ratio of the compound comprising Formula (IV) to the compound comprising Formula (IV') will range from about 0.5:1 to about 10:1. In some embodiments, the ratio of the compound comprising Formula (IV) to the compound comprising Formula (IV') may range from about 0.5:1 to about 2:1, from about 2:1 to about 4:1, from about 4:1 to about 6:1, from about 6:1 to about 8:1, or from about 8:1 to about 10:1.

comprising Formula (IIa) is about 0.01:1; and the molar ratio of the compound comprising Formula (IIa) to formic acid to triethylamine ranges from about 1:4:2 to about 1:6:3. A mixture of isopropyl alcohol and tetrahydrofuran is added to the precipitated compound comprising Formula (IIIa), which is reduced by contact with lithium metal and liquid ammonia at about −70° to about −60° C. to form the compound comprising Formula (IVa). The molar ratio of the compound comprising Formula (IIIa) to lithium ranges from about 1:3 to about 1:10; and the weight to volume ratio of the compound comprising Formula (IIIa) to liquid ammonia ranges from about 1:3 to about 1:10 (g/mL). For the purpose of illustration, Reaction Scheme 2 depicts this aspect of the invention:

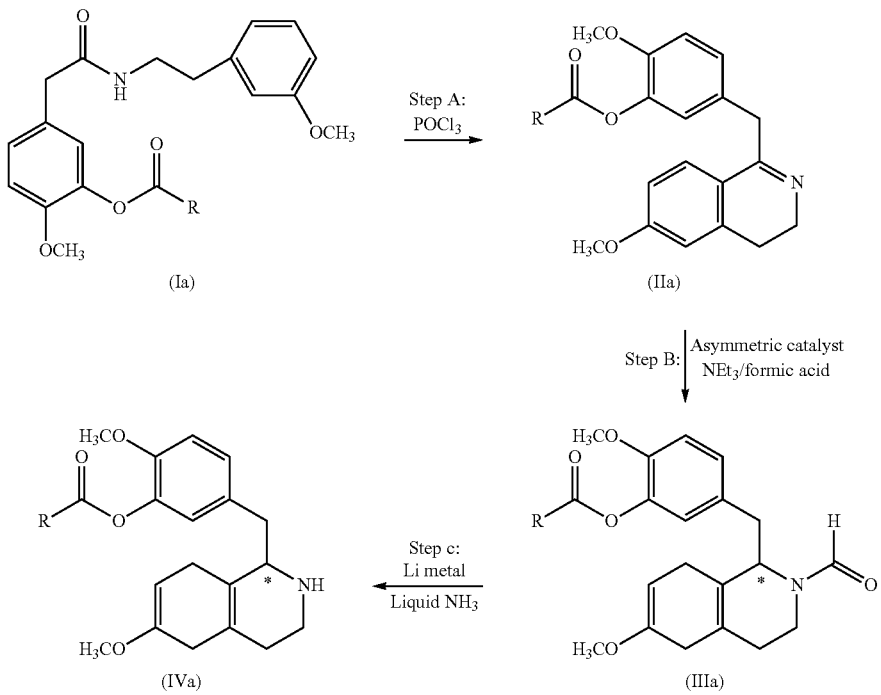

Reaction Scheme 2:

Upon completion of the reaction, the hexahydroisoquinoline comprising Formula (IV) may isolated by any method known to one skilled in the art. The compound comprising Formula (IV) may be utilized in other reactions, e.g., for the preparation of morphinans and analogs thereof.

(IV) Preferred Embodiment

In a preferred embodiment, a compound comprising Formula (Ia) is dissolved in toluene and contacted with about one molar equivalent of $POCl_3$ at room temperature to form a compound comprising Formula (IIa). After removal of the toluene, acetonitrile is added to the compound comprising Formula (IIa), which is then reacted at room temperature with an asymmetric catalyst comprising dichloro(p-cymene) ruthenium(II) dimer and either (1S,2S)-(+)-p-toluenesulfonyl-1,2-diphenylethylenediamine or (1R,2R)-(+)-p-toluenesulfonyl-1,2-diphenylethylenediamine, triethylamine, and formic acid to form the compound comprising Formula (IIIa). The weight ratio of the asymmetric catalyst to the compound wherein:
R is alkyl or aryl.
In exemplary embodiments, R is methyl, t-butyl, or phenyl.
In some embodiments, the asymmetric reduction of step B may also produce a compound comprising Formula (IIIa'):

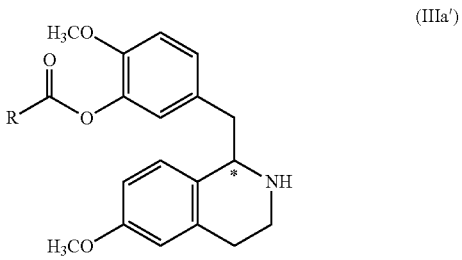

wherein R is as defined above in Reaction Scheme 2.
In still other embodiments, the Birch reduction of step C may also yield a compound comprising Formula (IVa'):

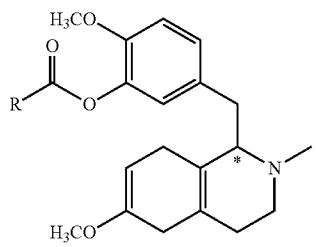

(IVa′)

wherein R is as defined above in Reaction Scheme 2.

(V) Stereochemistry

The tetrahydroisoquinoline and hexahydroisoquinoline compounds prepared by the processes of the invention are optically active compounds. The chiral carbon may have an R or an S configuration. Accordingly, each compound may comprise a (+) or a (−) orientation with respect to the rotation of polarized light.

DEFINITIONS

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as park of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl(Ph), biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β methoxyethoxymethyl (MEM), tetrahydropyranyl (THP), ethoxy ethyl (EE), methylthiomethyl (MTM), 2 methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, Fourth Edition, 2007.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amino, acetal, carbamyl, carbocyclo, cyano, ester, ether, halogen, heterocycle, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Preparation of Compound 7-Pivaloyl from Compound 5-Pivaloyl

The following reaction scheme depicts the synthesis of compound 7-pivaloyl:

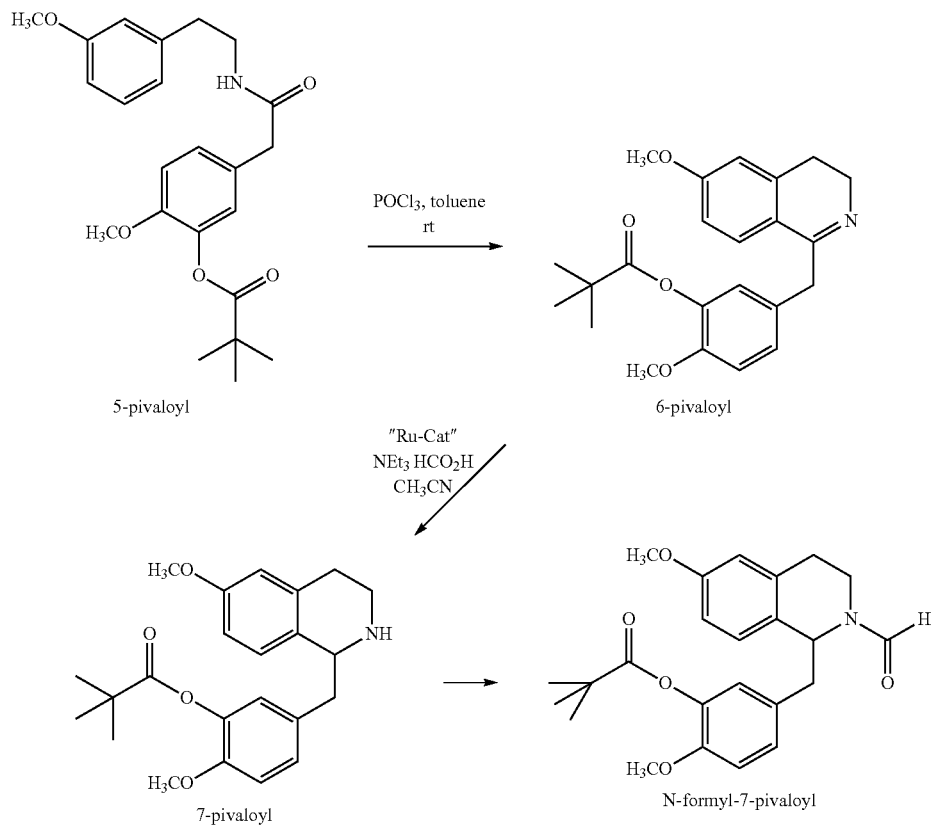

The amide, compound 5-pivaloyl (28.00 g, 0.07 moles) was dissolved in 50 mL toluene. A short path distillation apparatus was attached to the reaction flask and approximately half of the reaction solvent was distilled off by applying house vacuum. The reaction mixture was cooled to room temperature. Then, using an addition funnel, phosphorus oxychloride (10.74 g, 0.07 moles, 6.53 mL) was added drop wise to the reaction mixture. Once the addition was complete, the reaction mixture was stirred at room temperature for 1 hour. After replacing the addition funnel with a short path distillation apparatus, the remainder of the solvent was distilled off leaving a brown residue comprising the dihydroisoquinoline, compound 6-pivaloyl. After cooling the solution to room temperature, acetonitrile (50 mL) was added to reaction flask containing compound 6-pivaloyl and the mixture was degassed using nitrogen gas. In a separate flask, triethylamine (23.48 g, 0.23 moles, 32.34 mL) and acetonitrile (50 mL) were added. Using an addition funnel, >96% formic acid (25.00 g, 0.54 moles, 20.49 mL) was added to the flask. This solution exothermed to 40° C. and was stirred for an additional 45 minutes until the temperature reached 25° C. The triethylammonium formate solution was added into the solution of compound 6-pivaloyl. After degassing the solution for an additional 15 minutes, dichloro(p-cymene) ruthenium (II) dimer (250 mg) and (1S,2S)-(+)-p-toluenesulfonyl-1,2-diphenylethylenediamine (250 mg) were added. This reaction mixture was stirred at room temperature for 16 hours. HPLC indicated the reaction was complete. The reaction mixture was filtered through a Buchner funnel, rinsing the funnel with acetonitrile (25 mL), and then concentrated to a thick oil. To the oil was added ethyl acetate (25 mL) and then heptane (20 mL). This solution was cooled to 5° C. Crystals formed which were isolated by filtration, rinsed with heptane, and then dried on the funnel producing the N-formyl-compound 7-pivoloyl (8.20 g, 28.4% yield). The filtrate was evaporated to a thick oil containing N-formyl-compound 7-pivoloyl (major product) and NH-compound 7-pivoloyl (minor product).

Example 2

Preparation of Compound 7-Acetyl from Compound 5-Acetyl

The preparation of compound 7-acetyl is depicted in the following reaction scheme:

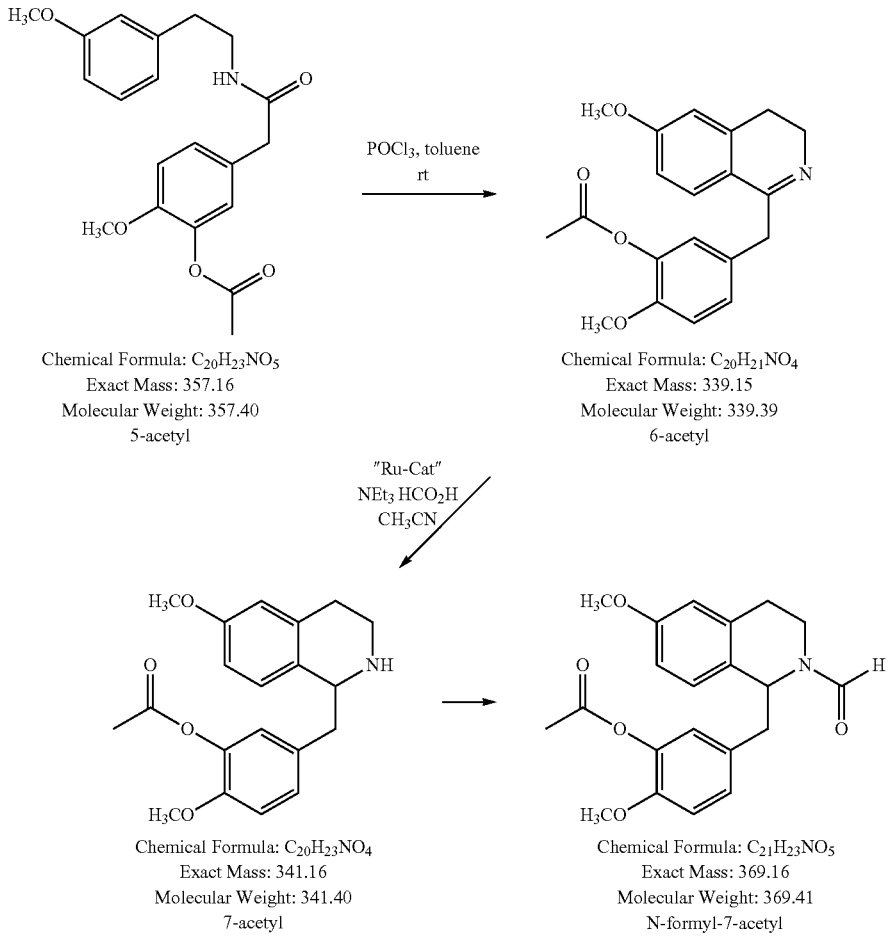

The amide, compound 5-acetyl (25.00 g, 0.07 moles) was dissolved in 50 mL toluene. A short path distillation apparatus was attached to the reaction flask and approximately half of the reaction solvent was distilled off by applying house vacuum. The reaction mixture was cooled to room temperature. Then, using an addition funnel, phosphorus oxychloride (10.72 g, 0.07 moles, 6.52 mL) was added drop wise. Once the addition was complete, the reaction mixture was stirred at room temperature for 1 hour. After replacing the addition funnel with a short path distillation apparatus, the remainder of the solvent was distilled off leaving a brown residue comprising the compound 6-acetyl. After cooling to room temperature, acetonitrile (25 mL) was added to the reaction flask containing compound 6-acetyl and the mixture was degassed using nitrogen gas. Triethylamine (23.53 g, 0.23 moles, 32.27 mL) and acetonitrile (50 mL) were added to a separate flask. Using an addition funnel, >96% formic acid (24.95 g, 0.54 moles, 20.45 mL) was added to the flask. This solution exothermed to 40° C. and was stirred for an additional 45 minutes until the temperature reached 25° C. The triethylammonium formate solution was added into the solution of compound 6-acetyl. After degassing the solution for an additional 15 minutes, dichloro(p-cymene) ruthenium (II) dimer (250 mg) and (1S,2S)-(+)-p-toluenesulfonyl-1,2-diphenylethylenediamine (250 mg) were added. This reaction stirred at room temperature for 16 hours. HPLC indicated the reaction was complete. The reaction mixture was filtered through a Buchner funnel, the funnel was rinsed with acetonitrile (25 mL), and the filtrate was concentrated to a thick oil (24.60 g) comprising a mixture of N-formyl-compound 7-acetyl (major product) and NH-compound 7-acetyl (minor product).

Example 3

Preparation of Compound 8 from N-Formyl-Compound 7-Acetyl

The following reaction scheme depicts the synthesis of compound 8:

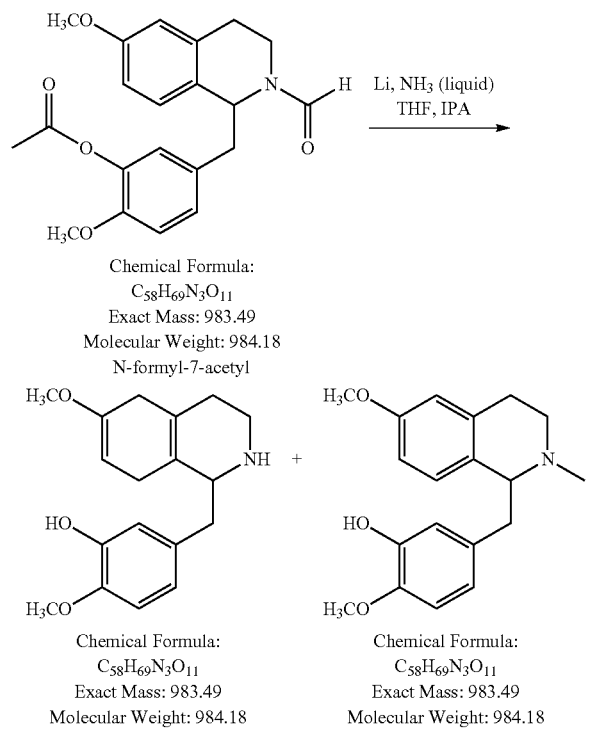

N-formyl-compound 7-acetyl (16.30 g, 0.04 moles) was dissolved in anhydrous tetrahydrofuran (THF) (50 mL) and isopropanol (10 mL) then transferred into a 3 neck round bottom flask. The reaction flask was cooled to −70° C. (CO$_2$/acetone) and a dry ice condenser was attached. To the reaction flask was added condensed liquid ammonia (~100 mL). To this reaction mixture was added lithium metal (3.08 g, the lithium metal was rinsed with heptane before use) in 3 portions over 1 hour. The reaction mixture was stirred for 30 minutes at −70 to −60° C. Then, anhydrous methanol (15 mL) was added drop wise. After stirring for 1 hour, the low temperature bath was removed and the reaction was warmed to room temperature by stirring for 1 hour after a nitrogen purge. Then distilled water (100 mL) was added to the mixture, and it was stirred for 1 hour. A precipitate formed. The precipitate was removed by filtration and dried on a funnel. The solid (12 g) contained a mixture of compound 8 and the N-methyl analog.

What is claimed is:

1. A one-pot process for the preparation of a compound comprising Formula (IV), the process comprising:
    (a) contacting a compound comprising Formula (I) with POCl$_3$ to form a compound comprising Formula (II);
    (b) contacting the compound comprising Formula (II) with an asymmetric catalyst and a hydrogen donor comprising a formate ion to form a compound comprising Formula (III); and
    (c) contacting the compound comprising Formula (III) with an alkali metal and an electron source to form the compound comprising Formula (IV) according to the following reaction scheme:

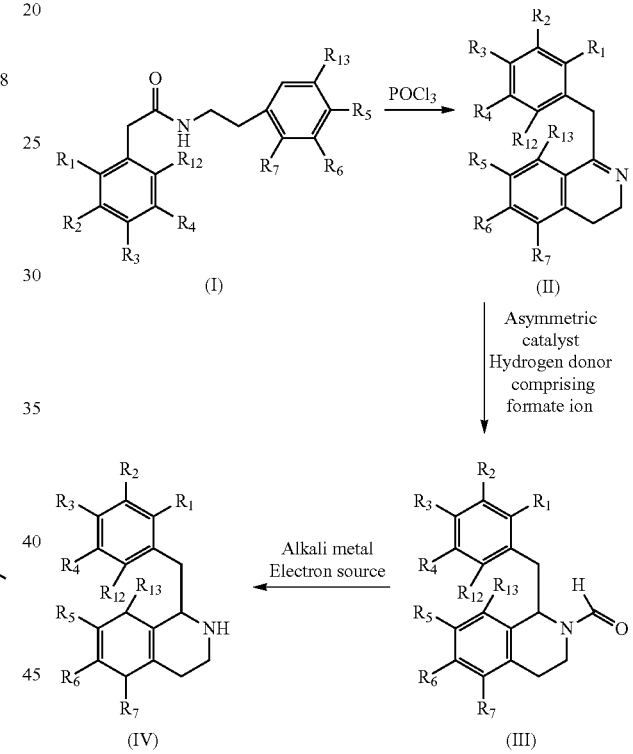

wherein:
    $R_1$, $R_5$, and $R_7$ are independently chosen from hydrogen, hydrocarbyl, substituted hydrocarbyl, and —OR$_{111}$;
    $R_2$, $R_4$, and $R_6$ are independently chosen from hydrogen, hydrocarbyl, substituted hydrocarbyl, halo, and —OR$_{211}$;
    $R_3$ is chosen from hydrogen, hydrocarbyl, substituted hydrocarbyl, and —OR$_{211}$;
    $R_{12}$ and $R_{13}$ are independently chosen from hydrogen, hydrocarbyl, substituted hydrocarbyl, halo, and —OR$_{111}$;
    $R_{111}$ is chosen from hydrogen, hydrocarbyl, and substituted hydrocarbyl;
    $R_{211}$ is chosen from hydrogen, hydrocarbyl, —C(O)R$_{212}$, —C(O)C(R$_{212}$)$_3$, —C(O)NHR$_{212}$, and —SO$_2$R$_{212}$; and
    $R_{212}$ is chosen from hydrocarbyl and substituted hydrocarbyl, and further wherein (i) the compound comprising Formula (II) is not isolated as a solid prior to step (b) and (ii) the compound comprising Formula (III) is not isolated as a solid prior to step (c).

2. The process of claim 1, wherein a compound comprising Formula (III') is also formed during step (b):

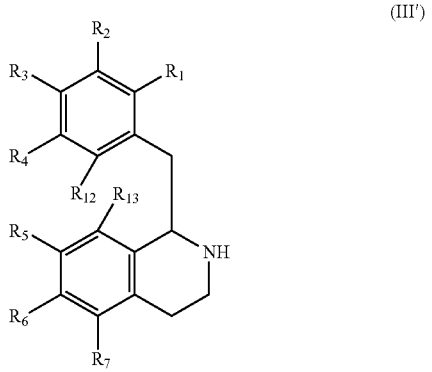

(III')

wherein:
- $R_1$, $R_5$, and $R_7$ are independently chosen from hydrogen, hydrocarbyl, substituted hydrocarbyl, and $-OR_{111}$;
- $R_2$, $R_4$, and $R_6$ are independently chosen from hydrogen, hydrocarbyl, substituted hydrocarbyl, halo, and $-OR_{211}$;
- $R_3$ is chosen from hydrogen, hydrocarbyl, substituted hydrocarbyl, and $-OR_{211}$;
- $R_{12}$ and $R_{13}$ are independently chosen from hydrogen, hydrocarbyl, substituted hydrocarbyl, halo, and $-OR_{111}$;
- $R_{111}$ is chosen from hydrogen, hydrocarbyl, and substituted hydrocarbyl;
- $R_{211}$ is chosen from hydrogen, hydrocarbyl, $-C(O)R_{212}$, $-C(O)C(R_{212})_3$, $-C(O)NHR_{212}$, and $-SO_2R_{212}$; and
- $R_{212}$ is chosen from hydrocarbyl and substituted hydrocarbyl.

3. The process of claim 1, wherein a compound comprising Formula (IV') is also formed during step (c):
wherein:

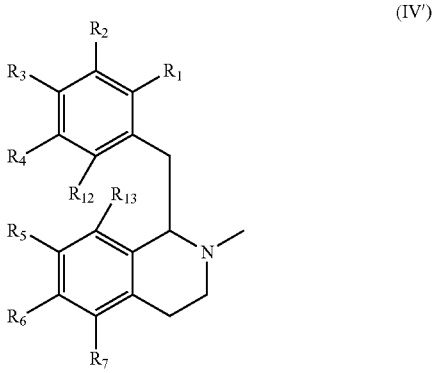

(IV')

- $R_1$, $R_5$, and $R_7$ are independently chosen from hydrogen, hydrocarbyl, substituted hydrocarbyl, and $-OR_{111}$;
- $R_2$, $R_4$, and $R_6$ are independently chosen from hydrogen, hydrocarbyl, substituted hydrocarbyl, halo, and $-OR_{211}$;
- $R_3$ is chosen from hydrogen, hydrocarbyl, substituted hydrocarbyl, and $-OR_{211}$;
- $R_{12}$ and $R_{13}$ are independently chosen from hydrogen, hydrocarbyl, substituted hydrocarbyl, halo, and $-OR_{111}$;
- $R_{111}$ is chosen from hydrogen, hydrocarbyl, and substituted hydrocarbyl;
- $R_{211}$ is chosen from hydrogen, hydrocarbyl, $-C(O)R_{212}$, $-C(O)C(R_{212})_3$, $-C(O)NHR_{212}$, and $-SO_2R_{212}$; and
- $R_{212}$ is chosen from hydrocarbyl and substituted hydrocarbyl.

4. The process of claim 1, wherein:
- $R_3$ is $-OR_{211}$;
- $R_{211}$ is chosen from hydrogen, alkyl, $-C(O)R_{212}$, $-C(O)C(R_{212})_3$, $-C(O)NHR_{212}$, and $-SO_2R_{212}$; and
- $R_{212}$ is chosen from alkyl and aryl.

5. The process of claim 1, wherein:
- $R_4$ is $-OR_{211}$;
- $R_{211}$ is chosen from hydrogen, alkyl, $-C(O)R_{212}$, $-C(O)C(R_{212})_3$, $-C(O)NHR_{212}$, and $-SO_2R_{212}$; and
- $R_{212}$ is chosen from alkyl and aryl.

6. The process of claim 1, wherein:
- $R_6$ is $-OR_{211}$;
- $R_{211}$ is chosen from hydrogen, alkyl, $-C(O)R_{212}$, $-C(O)C(R_{212})_3$, $-C(O)NHR_{212}$, and $-SO_2R_{212}$; and
- $R_{212}$ is chosen from alkyl and aryl.

7. The process of claim 1, wherein $R_1$, $R_2$, $R_5$, $R_7$, $R_{12}$, and $R_{13}$ are hydrogen; $R_3$ and $R_6$ are methoxy; $R_4$ is chosen from hydroxyl, $-OC(O)CH_3$, $-C(O)C(CH_3)_3$, $-OC(O)Ph$, and $-OSO_2CH_3$; $R_{12}$ is chosen from alkyl, allyl, benzyl, and halo; and $R_{212}$ is methyl.

8. The process of claim 1, wherein:
- $R_3$, $R_4$, and $R_6$ are $-OR_{211}$;
- $R_{211}$ is chosen from hydrogen, alkyl, $-C(O)R_{212}$, $-C(O)C(R_{212})_3$, $-C(O)NHR_{212}$, and $-SO_2R_{212}$; and
- $R_{212}$ is chosen from alkyl and aryl.

9. The process of claim 1, wherein the molar ratio of the compound comprising Formula (I) to $POCl_3$ is from about 1:0.5 to about 1:5.

10. The process of claim 1, wherein the asymmetric catalyst comprises a metal or a metal source and a chiral ligand.

11. The process of claim 10, wherein the metal or metal source is chosen from ruthenium, a ruthenium complex, osmium, an osmium complex, rhodium, a rhodium complex, iridium, an iridium complex, palladium, a palladium complex, platinum, a platinum complex, and combinations thereof; and the chiral ligand is a compound chosen from Formula 670, Formula 680, Formula 690, and Formula 700:

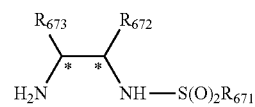

670

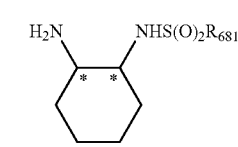

680

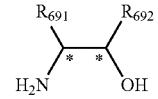

690

-continued

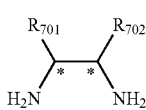

700 wherein:

$R_{671}$, $R_{672}$, $R_{673}$, $R_{681}$, $R_{691}$, $R_{692}$, $R_{701}$, and $R_{702}$ are independently alkyl or aryl; and $R_{671}$, $R_{672}$, and $R_{673}$ are independently alkyl or aryl; and $R_{691}$ and $R_{692}$ of Formula 690 and $R_{701}$ and $R_{702}$ of Formula 700, and the carbon atoms to which they are attached, may optionally form a cyclic or bicyclic compound.

12. The process of claim 10, wherein the metal source is dichloro(p-cymene) ruthenium(II) dimer and the chiral ligand is (1S,2S)-(+)-N-4-tolylsulfonyl-1,2-diphenylethylene-1,2-diamine.

13. The process of claim 1, wherein the weight ratio of the asymmetric catalyst to the compound comprising Formula (II) is about 0.001:1 to about 0.1:1; the molar ratio of the compound comprising Formula (II) to the hydrogen donor is about 1:1 to about 1:20.

14. The process of claim 1, wherein the hydrogen donor is chosen from formic acid, a salt of formic acid, and a mixture of formic acid and an organic base.

15. The process of claim 1, wherein the hydrogen donor comprises formic acid and triethylamine.

16. The process of claim 1, wherein the alkali metal is chosen from lithium, sodium, and potassium; and the electron source is chosen from liquid ammonia, methylamine, ethylamine, ethylenediamine, and combinations thereof.

17. The process of claim 1, wherein the alkali metal is lithium and the electron source is liquid ammonia.

18. The process of claim 1, wherein the molar ratio of the compound comprising Formula (III) to the alkali metal is from about 1:2 to about 1:20; and the weight to volume ratio of the compound comprising Formula (III) to the electron source is from about 1:2 to about 1:50 (g/mL).

19. The process of claim 1, wherein steps (a) and (b) are conducted at a temperature from about 20° C. to about 100° C., and step (c) is conducted at a temperature from about −80° C. to about 10° C.; and the compound comprising Formula (IV) has a yield of at least about 60%.

20. The process of claim 1, wherein the molar ratio of the compound comprising Formula (I) to $POCl_3$ is about 1:1; the asymmetric catalyst comprises dichloro(p-cymene) ruthenium(II) dimer and either (1S,2S)-(+)-N-4-tolylsulfonyl-1,2-diphenylethylene-1,2-diamine or (1R,2R)-(+)-N-4-tolylsulfonyl-1,2-diphenylethylene-1,2-diamine; the weight ratio of the asymmetric catalyst to the compound comprising Formula (II) is about 0.01:1; the hydrogen donor comprises formic acid and triethylamine; the molar ratio of the compound comprising Formula (II) to formic acid to triethylamine is from about 1:4:2 to about 1:6:3; the alkali metal is lithium and the electron source is liquid ammonia; the molar ratio of the compound comprising Formula (III) to lithium is from about 1:3 to about 1:10; the weight to volume ratio of the compound comprising Formula (III) to liquid ammonia is from about 1:3 to about 1:10 (g/mL); steps (a) and (b) are conducted at a temperature from about 22° C. to about 25° C.; step (c) is conducted at a temperature from about −70° C. to about −60° C.; and the compound comprising Formula (IV) has a yield of at least about 60%.

* * * * *